United States Patent [19]
Kubela et al.

[11] Patent Number: 5,908,959
[45] Date of Patent: Jun. 1, 1999

[54] PROCESS FOR THE PRODUCTION OF 4-AMINO-1-HYDROXYBUTYLIDENE-1,1-BISPHOSPHONIC ACID OR SALTS THEREOF

[75] Inventors: Rudolf Kubela, Stouffville; Yong Tao, Richmond Hill, both of Canada

[73] Assignee: Apotex Inc., Weston, Canada

[21] Appl. No.: 09/019,806

[22] Filed: Feb. 6, 1998

[30] Foreign Application Priority Data

Feb. 11, 1997 [CA] Canada .................................. 2197267

[51] Int. Cl.⁶ ...................................................... C07F 9/30
[52] U.S. Cl. ................................................ 562/13; 562/10
[58] Field of Search ........................................ 562/11, 13

[56] References Cited

U.S. PATENT DOCUMENTS

| | | |
|---|---|---|
| 4,157,364 | 6/1979 | Buckman . |
| 4,304,734 | 12/1981 | Jary . |
| 4,407,761 | 10/1983 | Blum et al. ........................... 260/502.5 |
| 5,019,651 | 5/1991 | Kieczykowski ............................. 562/13 |
| 5,510,517 | 4/1996 | Dauer ........................................ 562/13 |

FOREIGN PATENT DOCUMENTS

| | | |
|---|---|---|
| 2018477 | 8/1995 | Canada . |
| 2044923 | 6/1996 | Canada . |

OTHER PUBLICATIONS

Kieczykowski et al., "Preparation of (4–Amino–1–Hydroxybutylidene)bisphosphonic Acid Sodium Salt, MK–217 (Alendronate Sodium). An Improved Procedure for the Preparation of 1–Hydroxy–1,1–bisphosphonic Acids", *J. Org. Chem.,* 1995, vol. 60, pp. 8310–8312.

*Primary Examiner*—Gary Geist
*Assistant Examiner*—Jean F Vollano
*Attorney, Agent, or Firm*—Ivor M. Hughes; Neil H. Hughes; Marcelo K. Sarkis

[57] ABSTRACT

A process is provided for the preparation of 4-amino-1-hydroxybutylidene-1,1-bisphosphonic acid or salts thereof which comprises of:

a) reacting 4-aminobutyric acid with phosphorous acid and phosphorus trichloride in the presence of a polyalkylene(glycol); and b) recovering said 4-amino-1-hydroxybutylidene-1,1-bisphosphonic acid or salts thereof.

11 Claims, No Drawings

PROCESS FOR THE PRODUCTION OF 4-AMINO-1-HYDROXYBUTYLIDENE-1,1-BISPHOSPHONIC ACID OR SALTS THEREOF

BACKGROUND OF THE INVENTION

This invention relates to an improved industrial process for the preparation of 4-amino-1-hydroxybutylidene-1,1-bisphosphonic acid or salts thereof, in which the end product is obtained in a exceptionally pure form.

Several methods have been reported for preparation of ω-amino-1-hydroxyalkylidene-1,1-bisphosphonic acids in general and 4-amino-1-hydroxybutylidene-1,1-bisphosphonic acid in particular. The syntheses basically consist of reacting the corresponding ω-amino acid with a mixture of phosphorous acid and one of the three phosphorus chlorides—phosphorus trichloride, phosphorus oxychloride or phosphorus pentachloride, then quenching the reaction mixture with water or a non-oxidizing aqueous acid followed by heating to hydrolyse the phosphorous intermediates to the final product.

U.S. Pat. No. 4,407,761 (Blom et al.) to Henkel Kommanditgesellschaft teaches how to prepare also 4-amino-1-hydroxybutylidene-1,1-bisphosphonic acid beside other bisphosphonic acids. The reaction is carried out at about 100° C. in chlorobenzene as a diluent which does not solubilize the reaction components and serves only as a heat carrier. The reaction starts as a two phase system, in which the melt gradually thickens into a non-stirrable mass. This semisolid sticky mass finally turns into a hard, rigid material coated on the walls of the reaction vessel which is preventing smooth heat transfer. The process might be suitable for laboratory preparation of gram quantities of the product, however, for industrial production it is not acceptable and is not reasonable even for a modest scaleup.

The above described flaws of the process were acknowledged by Kieczykowski et al., who in Application For Canadian Patent 2,018,477 and 2,044,923 to Merck & Co. revealed a solution to the solidification problem. Methanesulfonic acid was used to solubilize the reaction components and keep it fluid up to completion of the reaction. Although the problems with physical characteristics of the reaction were solved, a safety problem surfaced. Methanesulfonic acid reacts with phosphorus trichloride and under adiabatic conditions the reaction becomes self-heating at 85° C. and an uncontrolled exotherm occurs at >140° C. This fact was recognized by the authors of the invention and in Example 1 of both Applications For Canadian Patent (2,018,477 and 2,044,923) caution is raised. The safety concern in somewhat more detail is mentioned by the authors (Kieczykowski et al.) in an article of J. Org. Chem. 1995, 60, 8310–8312.

The present invention solves both, the solidification and the safety problems by the use of a poly(alkylene glycol) or its derivative. Poly(alkylene glycols) solubilize the reaction components and do not react with the reactants to cause any uncontrolled reactions. The process is suitable for commercial manufacturing and can be scaled to large vessels with no danger of temperature escalation. The reaction can be carried out also at elevated temperatures. Since polyalkylene glycols and its derivatives are soluble in water, the reaction mixture can be quenched into water, the intermediates subsequently hydrolysed and the final product directly isolated.

SUMMARY OF THE INVENTION

The present invention provides a process for the preparation of 4-amino-1-hydroxybutylidene-1,1-bisphosphonic acid or salts thereof which comprises:

(a) reacting 4-aminobutyric acid with a mixture of phosphorous acid and phosphorus trichloride in a solution of a poly(alkylene glycol) or its derivatives at a suitable temperature such as between about 45° C. and about 150° C.; and (b) hydrolysing the phosphorous intermediates by heating the reaction mixture in the presence of water and recovering the said 4-amino-1-hydroxybutylidene-1,1-bisphophonic acid or salts thereof.

The poly(alkylene glycol) or its derivatives may be selected from a poly(alkylene glycol) of general formula $R_1O-(Q-CH_2O-)_nR_2$, wherein $R_1$ and $R_2$ are different or the same and represent a hydrogen atom, a lower alkyl or lower acyl, Q is $-CH(CH_3)$ or $-CH_2$ and n is a number of between 4 and about 250. A preferred such compound is poly(ethylene glycol).

It has been found that 4-amino-1-hydroxybutylidene-1,1-biphosphonic acid can be obtained in a safe manner, in high yield and purity when using the present procedure of the invention. The main feature of the invention is in the use of a poly(alkylene glycol) or its derivatives in the phosphonylation reaction. The presence of such polymers facilitates the solubilization of the reaction components and keeps the mixture in homogenous form from start to completion of the reaction. The hydrolysis of the formed phosphorous intermediates can be completed in the same reaction mixture and if desired, by adjusting the pH to about 4.3, the sodium salt of the said biphosphonic acid can be directly obtained and isolated in a pure form and, if necessary, can be recrystallized from hot water.

The 4-aminobutyric acid and the phosphorous acid are suspended in a poly(alkylene glycol) or its derivative and reacted with phosphorus trichloride at a suitable temperature for example, between about 45° C. and 150° C., preferably at about 70° C., at which temperature the phosphonylation reaction is completed in about 3 hours. The preferred ratio of the amino acid to phosphorous acid and to phosphorus trichloride is about 1:1:2. To reduce the viscosity of the reaction mixture, an inert solvent may be used as diluent, however, this is not essential as it does not affect the yield or purity of the final product. If desired, these diluents can be added at any stage of the phosphonylation reaction.

As example of poly(alkylene glycols) which can be applied, are poly(ethylene glycol) and poly(propylene glycol) of average M.V. from about 200 to about 10,000. The terminal hydroxy groups of poly(alkylene glycols) can be unprotected or one or both of them protected as lower alkyl ethers or esters.

The reaction can be shown schematically as follows:

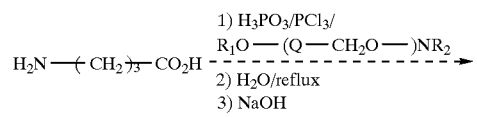

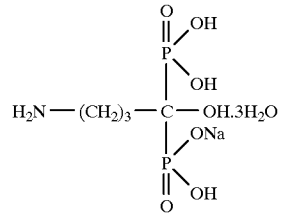

wherein $R_1$ and $R_2$ is the same or different and represents a hydrogen atom, a lower alkyl or acyl;

Q is $-CH_2-$ or $-CH(CH_3)-$ and n is a number between 4 and about 250.

The title compound in a pharmaceutical composition is useful for treatment of some bone disorders, such as osteoporosis and hypercalcemia of malignancy.

EXAMPLE 1

Preparation of 4-amino-1-hydroxybutylidene-1,1-biphosphonic Acid in PEG 400 Using Toluene as Diluent A 5 L flask was equipped with a mechanical stirrer, thermometer, condenser and a pressure equalized addition funnel. The system was connected to a caustic scrubber and flushed with nitrogen. The flask was charged with 830 g of PEG 400, 300 g (2.91 mol) of 4-aminobutyric acid and 230.5 g (2.91 mol) of phosphorous acid. After 15 minutes of stirring, with no heating or cooling bath, the reaction temperature of the mixture increased from 20° C. to 35° C. 750 mL of toluene was added at once, followed by dropwise addition of 405 mL (4.65 mol) phosphorus trichloride. In 30 minutes about 50% of the volume of $PCL_3$ were added and the internal temperature of the mixture increased to 50° C., when external heating was applied and the remaining of phosphorus trichloride was added continuously over a period of 30 minutes at internal temperature of 65° C. to 75° C. then aged at 75° C. for 4 hours. The mixture was cooled to 25° C., diluted with 900 mL of toluene and over 10 minutes added to a 5 L flask containing 1500 mL of vigorously stirred cold water. After completion of the addition the temperature of the two phase system reached 65° C. which was cooled to 25° C. The stirring was discontinued to allow the layers separate, the lower aqueous layer was transferred by means of vacuum into a 12 L flask and heated to reflux. 150 mL of distillate was collected to raise the internal temperature of the mixture to 105–106° C. After changing the position of the condenser, the mixture was refluxed for 4 hours, then cooled to 20° C. and with stirring, the product was precipitated as a white crystalline solid by slow addition of 3000 mL of acetone. The suspension was cooled to 0–3° C. and aged at this temperature for 5 hours. The product was collected by filtration, washed with 2×300 mL of cold (10–15° C.) 50% aqueous acetone. The yield after air drying at 50° C. was 453 g (58.3%).

Microchemical analysis, Calculated for $C_4H_{13}NO_7P_2 \cdot H_2O$: Theory: C 17.98%, H 5.66%, N 5.24%;
Found: C 18.08%, H 5.59%, N 5.14%.

EXAMPLE 2

Preparation of 4-amino-1-hydroxybutylidene-1,1-biphosphonic Acid in PEG 400 With No Diluent Present Starting with 100 g (0.97 mol) of 4-aminobutyric acid, 79.5 g (0.97 mol) of phosphorous acid and 176 mL (1.94 mol) of phosphorus trichloride in 277 g of PEG 400 in a 2 L flask, the experiment was conducted as described in Example 1 until the completion of the 4 hour aging at 75° C., except, no toluene was used to dilute the reaction mixture. The mixture was cooled to 20° C. and slowly, with vigorous stirring, in a period of 30 minutes, 500 mL of water was added with external air cooling only. The heat of dilution and decomposition of unreacted phosphorus starting materials caused the temperature of the reaction mixture to rise to 75° C. By means of an oil bath the mixture was heated to reflux (internal temperature 105–106° C.) and refluxed for 4 hours. After work up as described in Example 1, 152.0 g (58.7%) of the title product was obtained.

EXAMPLE 3

Preparation of 4-amino-1-hydroxybutylidene-1,1-biphosphonic Acid in Acetylated PEG Methyl Ether 350

A 5 L flask, equipped with a mechanical stirrer, thermometer, condenser and a pressure equalized addition funnel was connected to a caustic scrubber and the system flushed with nitrogen. The flask was charged with 700 g (2.0 mol) of poly(ethylene glycol) methyl ether 350. 145 mL (2.0 mol) of acetyl chloride was added dropwise over a period of 10 minutes and the temperature of the mixture rose from 20° C. to 48° C. After the mixture was cooled to 30° C., the flask was further charged with 200 g (1.94 mol) of 4-aminobutyric acid and 159 g (1.94 mol) of phosphorous acid. With no external cooling or heating applied the mixture was stirred for 50 minutes then 338 mL (3.88 mol) of phosphorus trichloride was added dropwise over a period of 35 minutes. After completion of the addition the internal temperature of the mixture was raised from 53° C. to 70° C. and aged for 4 hours. With external cooling, in a period of 1 hour, 1200 mL of water was cautiously added to the mixture, then it was heated to reflux (112° C.) for 3 hours. The content of the flask was cooled to 20° C. and added to 2000 mL of acetone (in a 12 L flask). Crystallization of the product was achieved by cooling the mixture to 3° C., seeding and aging it for 2 hours. The 4-amino-1-hydroxybutylidene-1,1-biphosphonic acid was collected by filtration, the cake washed with 2×250 mL ice cold 50% aqueous acetone and air dried at 50° C. to constant weight. The yield was 290.0 g (56.2%).

EXAMPLE 4

Preparation of 4-amino-1-hydroxybutylidene-1,1-biphosphonic Acid Monosodium Salt Trihydrate An experiment, on a scale of 36.1 g (0.35 mol) of 4-aminobutyric acid in a 1 L flask, was carried out up to completion of the 4 hour hydrolysis at 105–106° C. and cooling the mixture to 20° C., as described in Example 1. After, the pH of the solution was adjusted to 4.3 with 50% sodium hydroxide, at 20° C. two layers formed. The lower layer was separated, cooled to 2–3° C. and aged for 16 hours. The crystalline product was collected by filtration, washed with 2×75 mL of ice cold water and air dried at 50° C. The yield of 4-amino-1-hydroxybutylidene-1,1-biphosphonic acid was 66.0 g (58.0%).

Microchemical analysis, calculated for $C_4H_{12}NO_7P_2Na \cdot 3H_2O$:
Theory: C 14.77%, H 5.58%, N 4.31%;
Found: C 14.94%, H 5.48%, N 4.12%.

As many changes can be made to the embodiments without departing from the scope of the invention. It is intended that all material contained herein be treated as illustrative of the invention and not in a limiting sense.

What is claimed is:

1. A process for the preparation of 4-amino-1-hydroxybutylidene-1,1-biphosphonic acid or salts thereof which comprises of;
   (a) reacting 4-aminobutyric acid with a mixture of phosphorous acid and phosphorus trichloride in the presence of a poly(alkylene glycol) of general formula $R_1O$—$(Q$—$CH_2O$—$)_nR_2$, wherein $R_1$ and $R_2$ are different or the same and represent a hydrogen atom, a lower alkyl or lower acyl, Q is —$CH(CH_3)$ or —$CH_2$ and n is a number of between 4 and about 250; and
   (b) recovering said 4-amino-1-hydroxybutylidene-1,1-biphosphonic acid or salts thereof.

2. The process of claim 1 wherein said reaction is conducted in poly(ethylene glycol) of average M.W. 400.

3. The process of claim 2 wherein said reaction is carried out at temperature of from 45° C. to 150° C.

4. The process of claim 3 wherein 4-amino-1-hydroxybutylidene-1,1-biphosphonic acid or its salts thereof is recovered.

5. The process of making 4-amino-1-hydroxybutylidene-1,1-bisphosphonic acid and salts thereof by the use of poly(alkylene glycol) and its derivatives in a phosphonylation reaction.

6. The process of claim 5 wherein the poly(alkylene glycol) is poly(ethylene glycol).

7. The process of claim 6 wherein said reaction is conducted in poly(ethylene glycol) of average M.W. 400.

8. The process of claim 7 wherein said reaction is carried out at temperature of from 45° C. to 150° C.

9. The process of claim 8 wherein 4-amino-1-hydroxybutylidene-1,1-biphosphonic acid or its salts thereof is recovered.

10. The process of claim 1, 2, or 3 wherein the temperature is about 70° C.

11. The process of claim 5, 6, or 7 wherein the temperature is about 70° C.

* * * * *